US011172975B2

(12) United States Patent
Niedbala et al.

(10) Patent No.: US 11,172,975 B2
(45) Date of Patent: Nov. 16, 2021

(54) PORTABLE ELECTRO-MECHANICAL CRYOSURGICAL DEVICE

(71) Applicant: CRYOCONCEPTS LP, Bethlehem, PA (US)

(72) Inventors: R. Sam Niedbala, Bethlehem, PA (US); Philip Michael Formica, Bethlehem, PA (US); Lincoln C. Young, Bethlehem, PA (US)

(73) Assignee: CRYOCONCEPTS LP, Bethlehem, PA (US)

( * ) Notice: Subject to any disclaimer, the term of this patent is extended or adjusted under 35 U.S.C. 154(b) by 0 days.

(21) Appl. No.: 16/763,756

(22) PCT Filed: Nov. 16, 2018

(86) PCT No.: PCT/US2018/061585
§ 371 (c)(1),
(2) Date: May 13, 2020

(87) PCT Pub. No.: WO2019/099878
PCT Pub. Date: May 23, 2019

(65) Prior Publication Data
US 2020/0360070 A1    Nov. 19, 2020

Related U.S. Application Data

(60) Provisional application No. 62/587,709, filed on Nov. 17, 2017.

(51) Int. Cl.
*A61B 18/02* (2006.01)
*A61M 3/02* (2006.01)
(Continued)

(52) U.S. Cl.
CPC .......... *A61B 18/0218* (2013.01); *A61B 18/02* (2013.01); *A61B 2018/0047* (2013.01); *A61M 3/0258* (2013.01); *A61M 2039/226* (2013.01)

(58) Field of Classification Search
CPC ............... A61B 18/02; A61B 18/0218; A61B 2018/0231; A61B 2018/024;
(Continued)

(56) References Cited

U.S. PATENT DOCUMENTS 6,905,496 B1    6/2005  Ellman et al.
7,025,762 B2 *  4/2006  Johnston ............ A61B 18/0218
                                                600/104
(Continued)

OTHER PUBLICATIONS

PCT International Search Report and Written Opinion of International Application No. PCT/US2018/061585 dated Jan. 8, 2018.

*Primary Examiner* — Eun Hwa Kim
(74) *Attorney, Agent, or Firm* — J.A. Lindeman & Co. PLLC

(57) ABSTRACT

The portable cryosurgical device is economical, easy to use and operate, and delivers cryogenic material such as nitrous oxide and carbon dioxide gas in any direction or orientation. The delivered materials destroy target tissue using extremely cold temperatures and the abrasives formed when the cryogenic material becomes a solid. The device includes a portable countertop enclosure housing a cryogen source, a cryogen flow tube in fluid communication with the cryogen source, and a flow path assembly. The flow path assembly includes a valve between the cryogen source and the cryogen flow tube having substantially zero dead volume. The flow path assembly can include a quick-connect cryogen tank adapter and an in-line cryogen filter. The flow path assembly delivers liquefied compressed gas from the cryogen source to a terminal end of the cryogen flow tube without a phase change occurring in the flow path.

19 Claims, 12 Drawing Sheets

(51) Int. Cl.
*A61M 39/22* (2006.01)
*A61B 18/00* (2006.01)

(58) Field of Classification Search
CPC .... A61B 2018/0256; A61B 2018/0262; A61B 2018/0268; A61B 2018/0281; A61B 2018/0287; A61B 2018/0293; A61M 3/0258; A61M 2039/226
See application file for complete search history.

(56) References Cited

U.S. PATENT DOCUMENTS

| | | |
|---|---|---|
| 2002/0001046 A1 | 1/2002 | Joye et al. |
| 2002/0143323 A1 | 10/2002 | Johnston et al. |
| 2010/0094270 A1 | 4/2010 | Sharma |
| 2010/0184694 A1 | 7/2010 | Peled et al. |
| 2013/0184694 A1 | 7/2013 | Fourkas |
| 2013/0231651 A1 | 9/2013 | Burr et al. |
| 2015/0289920 A1 | 10/2015 | Burnett et al. |

* cited by examiner

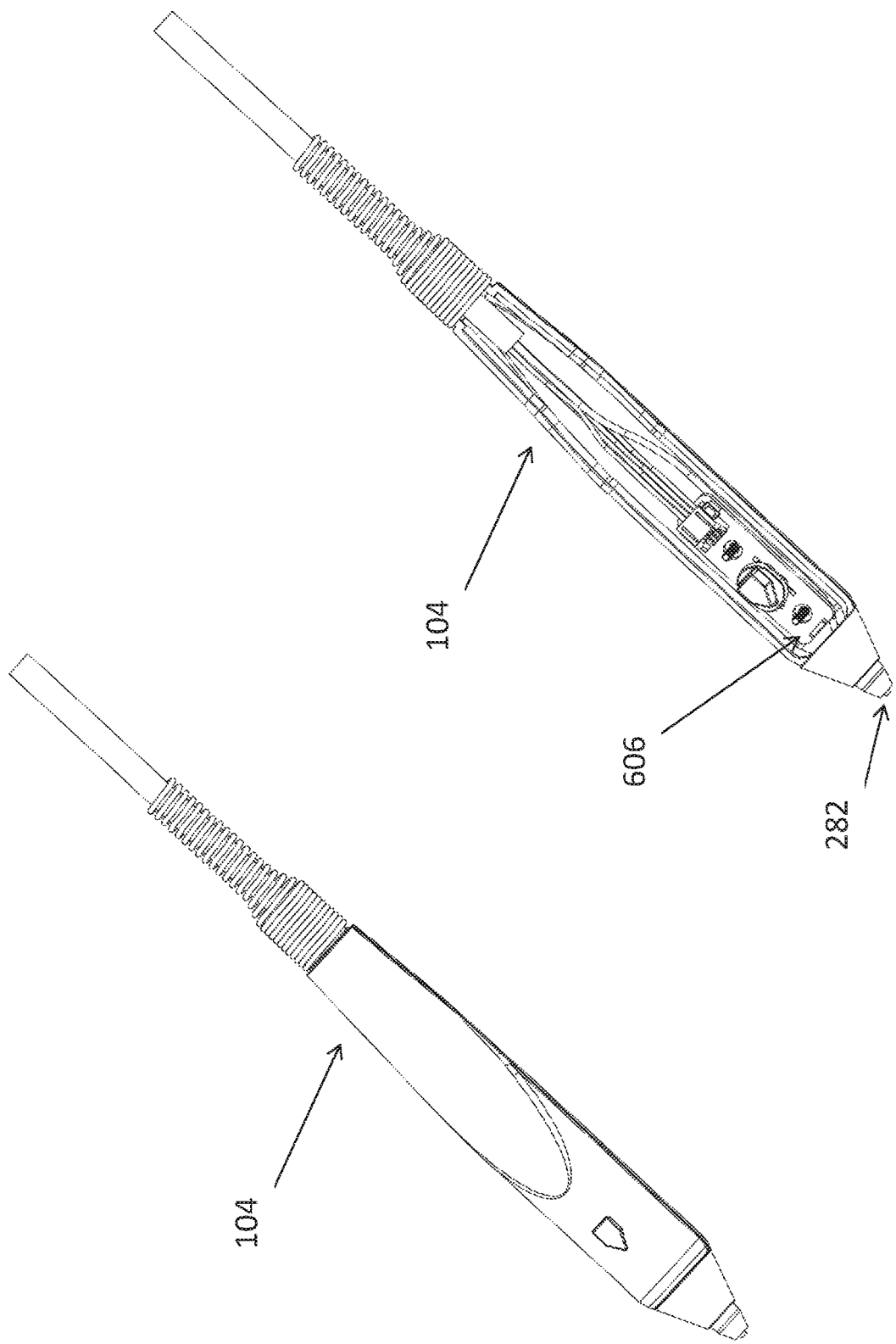

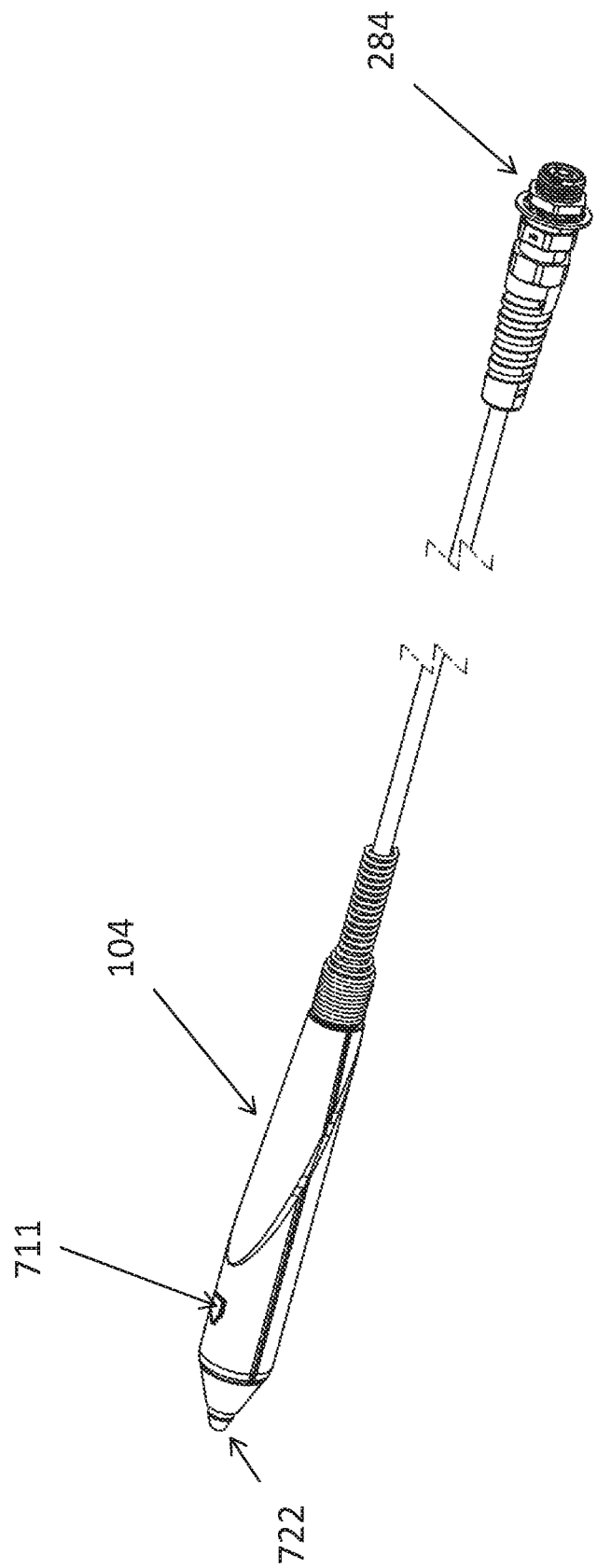

PORTABLE ELECTRO-MECHANICAL CRYOSURGICAL DEVICE

CROSS-REFERENCE TO RELATED APPLICATION

This application claims the benefit of U.S. Provisional Application No. 62/587,709, filed Nov. 17, 2017, the entire contents of which are incorporated herein by reference.

TECHNICAL FIELD

The invention relates to portable electro-mechanical devices. More specifically, the invention relates to cryogenic systems and methods for use in performing cryosurgical and cryogas spray procedures.

BACKGROUND

A number of procedures exist for treating superficial lesions on human and animal skin, some examples of which are as warts, achrocordon, sun spots, and age spots. Clinicians can remove such lesions through the localized freezing of the skin lesion tissue by using a cooling fluid, such as a liquid refrigerant. Direct spray methods for such localized freezing are governed by the "Joules Thomson" effect due to expansion of the cooling liquid. Physicians have used liquid nitrogen applications, for example, to freeze and remove lesions from a patient's skin. Conventional methods of treatment, however, often have the disadvantages of requiring specialized equipment to dispense the liquid nitrogen, the need for specialized storage devices, and the inherent hazards of handling and dispensing materials having very low boiling points, for example, as low as approximately −196° C. in the case of liquid nitrogen.

More recently, researchers have developed various methods to treat skin lesions cryosurgically by employing a cooling fluid (e.g., a cryogenic fluid) contained in a handheld pressurized container, for example. Such cryosurgical devices generally rely upon a liquefied (compressed) gas, such as butane, propane, or dimethyl ether (DME), and others to rapidly cool an applicator tip or "bud" based on the principles of "heat of vaporization." As the compressed gas flows to and contacts a surface of an applicator, such as a porous applicator bud, rapid evaporation of the gas causes the applicator surface to cool to temperatures that are lower than the boiling point of the liquefied gas alone. In several such methods, an effective amount of the cryogenic fluid from the pressurized container can be dispensed into a hollow supply tube having a cotton, fiber, and/or plastic foam bud located at the distal end of the supply tube. The cryogenic fluid accumulates in the applicator and upon evaporation, cools the applicator to temperatures well below freezing. The applicator then contacts the skin surface of the lesion for a period of time sufficient to reduce the temperature of the skin lesion tissue to temperatures that freeze the skin, such that permanent, irreversible rupture of the cellular membranes of the tissue occurs.

Cryosurgical devices currently utilizing the "heat of vaporization" principal in combination with compressed gases, such as dimethyl ether (DME) for example, may incur various types of complications. For example, the effectiveness of the devices can depend significantly upon the particular gas used, and rates of evaporation from the applicator may be relatively long (e.g., on the order of 15-30 seconds). Due to limited reservoirs for the applicator, the effective temperature of the applicator (i.e., the temperature of the applicator that is sufficient to cause freezing of the skin lesion) may be reached for only a short period of time, particularly once the applicator is placed in contact with the warmer surface of the skin lesion, thereby limiting effective freezing of the target tissue.

Various other cryosurgical devices utilize liquid nitrogen, or other liquefied gases such as, for example, chlorofluorocarbons or nitrous oxide, which have significantly lower boiling points and thus can be dispensed at colder temperatures than higher boiling point cryogens such as dimethyl ether (DME). Such cryosurgical devices, however, are generally still relatively complex in their structure, in that they use complicated valving mechanisms and dispensers to deliver the liquefied gas. Accordingly, problems can arise with such devices due to the high pressures exhibited by the gases, the complicated manner in which the cryogenic fluid is moved from the container to the dispensing tip of an applicator, the ease of use, and/or the cost associated with manufacture and/or assembly of the devices, resulting in high per-use costs.

Prior to the development of the present invention, there had yet to be developed cryosurgical devices that are both simple in structure and use, and that are capable of delivering a variety of cryogenic fluids, including more aggressive cooling agents, such as nitrous oxide, carbon dioxide, or other high pressure, low boiling point cryogens in an amount sufficient to achieve effective cryosurgical treatment.

Another complication of currently available cryosurgical devices is that the number of uses for each cryogenic device is often limited, resulting in high per-use costs for existing systems, as well as the miscalculation by system operators of treatment times. Additionally, some cryosurgical systems fail to indicate the number of treatments remaining for a given container of cryogenic liquid, with the potential result that the gas can run out mid-procedure. Additionally, with many portable cryosurgical treatment devices, the liquid gas flow is limited by gravity and therefore the device must be pointed downward to dispense cryogen properly. This often requires the patient/client to be positioned in awkward poses, with the result that the device valve is often difficult to actuate.

SUMMARY

The invention includes portable cryosurgical systems and methods for the application of cryogenic liquids, including carbon dioxide and nitrous oxide or similar high pressure, low boiling point gases. The invention provides cryosurgical destruction of unwanted skin lesions and dispenses cryogases for other purposes, such as aesthetics.

The invention provides a new platform that is economical, easy to use and operate, and delivers cryogenic material in any direction or orientation. The invention delivers many cryogenic materials to the patients' skin, including nitrous oxide and carbon dioxide gas. The delivered materials destroy target tissue using extremely cold temperatures and the abrasives formed when the cryogenic material becomes a solid.

The invention provides many additional benefits not previously realized by existing systems. The invention provides economical per-use costs over existing devices. The systems and methods of the invention provide measured and metered treatment times while providing an indication of the cryogen levels available for use. The system provides repeated uses and does not require disposable components. The system components of the invention are designed and manufactured to enable multi-direction application of the cryogens to affected areas and eliminates patient and clinician contortions. With the invention, clinicians can provide a focused application of cryogenic material to patients' affected areas. The small diameter application translates to a focused treatment spot and less damage to adjacent healthy tissue. Further, the device includes ergonomically-designed and manufactured actuation systems, including electro-mechanical valves and applicators.

The invention provides a measured delivery of cryogenic material to an affected area. For example, the system can be configured for 5- or 10-second treatment durations of a cryogen, including carbon dioxide or nitrous oxide, and other low boiling point pressurized gas intended to destroy unwanted skin lesions. Time settings as low as 1.0 second to a high setting of a continuous spray may be used. The application of the cryogenic materials to the patients' affected areas using varying times allows clinicians to customize freeze-and-thaw cycle times to optimize treatment of the affected areas. Clinicians can also use an illumination source on the tip of the wand to illuminate the treatment area for accurate delivery of the cryogenic material.

The invention includes a portable cryosurgical device including a portable countertop enclosure housing a cryogen source, a cryogen flow tube connected in fluid communication with the cryogen source, and a flow path assembly. The flow path assembly includes a solenoid valve positioned between the cryogen source and the cryogen flow tube and in fluid communication with the cryogen source and the cryogen flow tube. The solenoid valve includes a valve body with a valve seat, an inlet port on an inlet side of the valve seat that introduces the cryogen from the cryogen source into the valve body, an outlet port on an outlet side of the valve seat that receives the cryogen from the valve body, and a piston movable to cause the valve seat to move from a closed position preventing passage of the cryogen from the inlet side of the valve seat to the outlet side of the valve seat to an open position permitting the passage of the cryogen from the inlet side of the valve seat to the outlet side of the valve seat. In some example embodiments of the invention, the valve body from the inlet port to the outlet port includes a dead volume of less than 25 μL. In other example embodiments of the invention, the valve body from the inlet port to the outlet port includes a dead volume of less than 15 μL, and in other example embodiments of the invention, the valve body from the inlet port to the outlet port includes a dead volume of less than 1.5 μL.

In some embodiments of the invention, the flow path assembly can include a quick connect cryogen tank adapter that includes a pin valve receiver portion, a post, and a lever, and the pin valve receiver portion receives a pin valve of a cryogen tank and actuating the lever moves the post to press on a pin in a pin valve of the cryogen tank to open the pin valve to allow the cryogen to flow into the flow path assembly. Additionally, the adapter can include a vent that allows the cryogen in the flow path between the adapter and the solenoid valve to vent.

In some embodiments of the invention, the flow path assembly further includes an in-line cryogen filter that blocks foreign material from entering the solenoid valve while allowing the cryogen to flow freely. The flow path assembly can further deliver a liquefied compressed gas from the cryogen source to a terminal end of the cryogen flow tube without a phase change occurring in the flow path.

The portable cryosurgical device of the invention delivers a metered volume of cryogen based on a predetermined dispense time. Also, the volume of cryogen delivered can be further metered based on a flow rate through the cryogen flow tube. The flow rate through the cryogen flow tube can be based on length of the cryogen flow tube and/or inside diameter of the cryogen flow tube.

The portable countertop enclosure of the invention can include a treatment time selector, and the predetermined dispense time can be from one second to a continuous dispense.

The portable cryosurgical device of the invention can further include a dispensing wand that receives and houses the cryogen flow tube. The dispensing wand is omni-directional and delivers the cryogen from a wand tip independent of the orientation of the dispensing wand in relation to a target treatment area. In some embodiments of the invention, the dispensing wand delivers a liquid cryogen from the wand tip.

The portable cryosurgical device of the invention can have a cryogen source that is a single refillable cylinder, and the refillable cylinder can include an amount of liquid cryogen from twelve ounces to twenty ounces.

The portable cryosurgical device of the invention can include a cryogen source level indicating that provides an indication of an amount of the cryogen remaining in the cryogen source. The cryogen can be liquefied compressed gases at pressures of up to 850 psi. In some implementations of the invention, the cryogen can be liquid carbon dioxide, nitrous oxide, R125, and/or R410A.

In another implementation of the invention, the portable cryosurgical device includes a portable countertop enclosure housing a cryogen source, a cryogen flow tube connected in fluid communication with the cryogen source, a closed cryogen flow path assembly between the cryogen source and the cryogen flow tube and in fluid communication with the cryogen source and the cryogen flow tube that receives a cryogen from the cryogen source and provides the cryogen to the cryogen flow tube, and a dispensing wand that receives and houses the cryogen flow tube, where the dispensing wand is omni-directional and delivers the cryogen from a wand tip independent of the orientation of the dispensing wand in relation to a target treatment area.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6 shows two example wands for delivering cryogenic material using a portable electro-mechanical cryosurgical system in accordance with the invention.

FIG. 7 shows an example schematic diagram of a wand for delivering cryogenic material using the invention.

DETAILED DESCRIPTION

The portable electro-mechanical device of the invention provides applications of cryogenic materials to patient anatomical treatment areas for the cryosurgical destruction of unwanted skin lesions.

System Components

Figure 1:
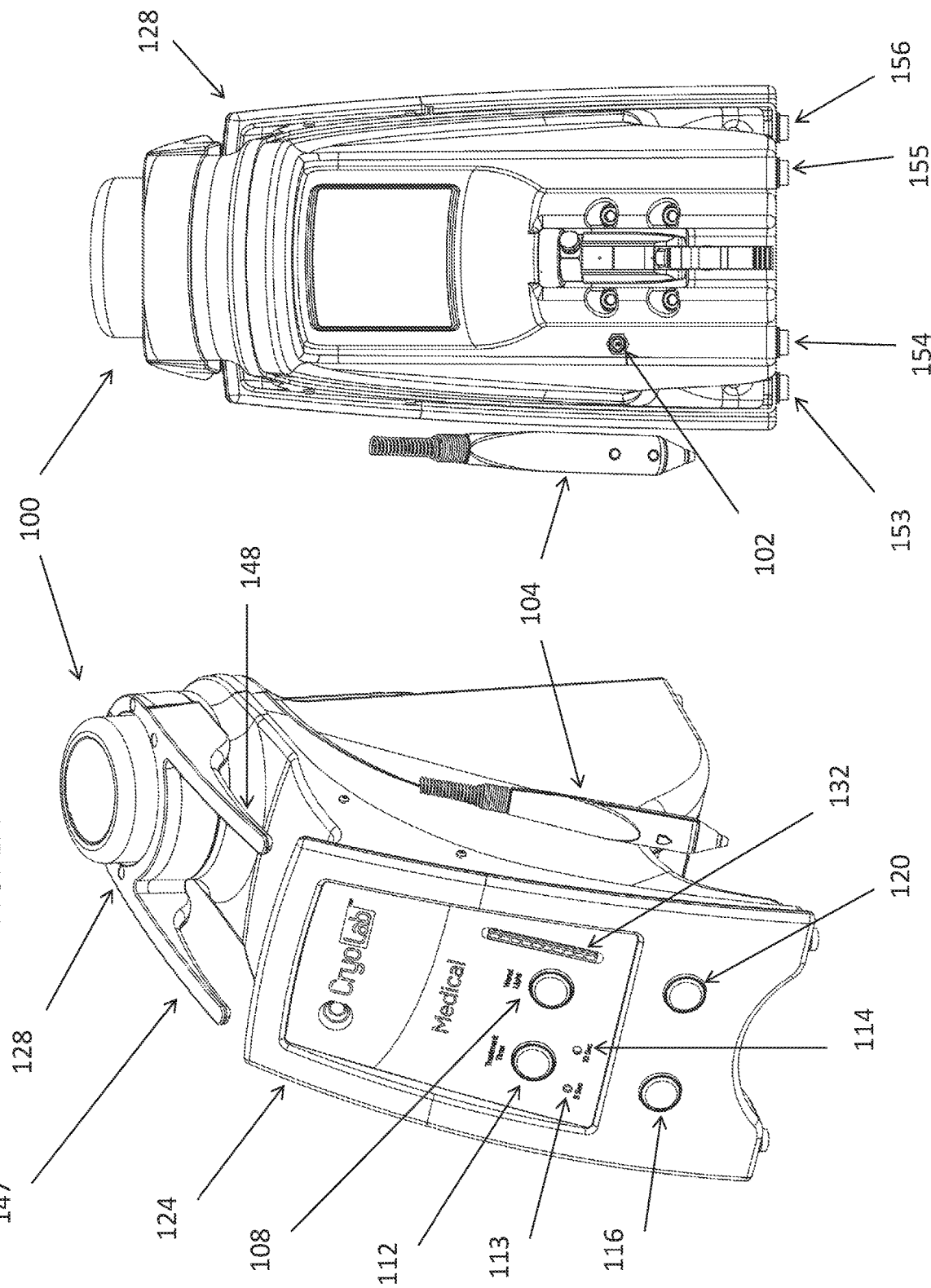
FIG. 1A shows a front view of a portable electro-mechanical cryosurgical system in accordance with the invention.
FIG. 1B shows a rear view of the portable electro-mechanical cryosurgical system in accordance with the invention of FIG. 1A.
Figure 2:
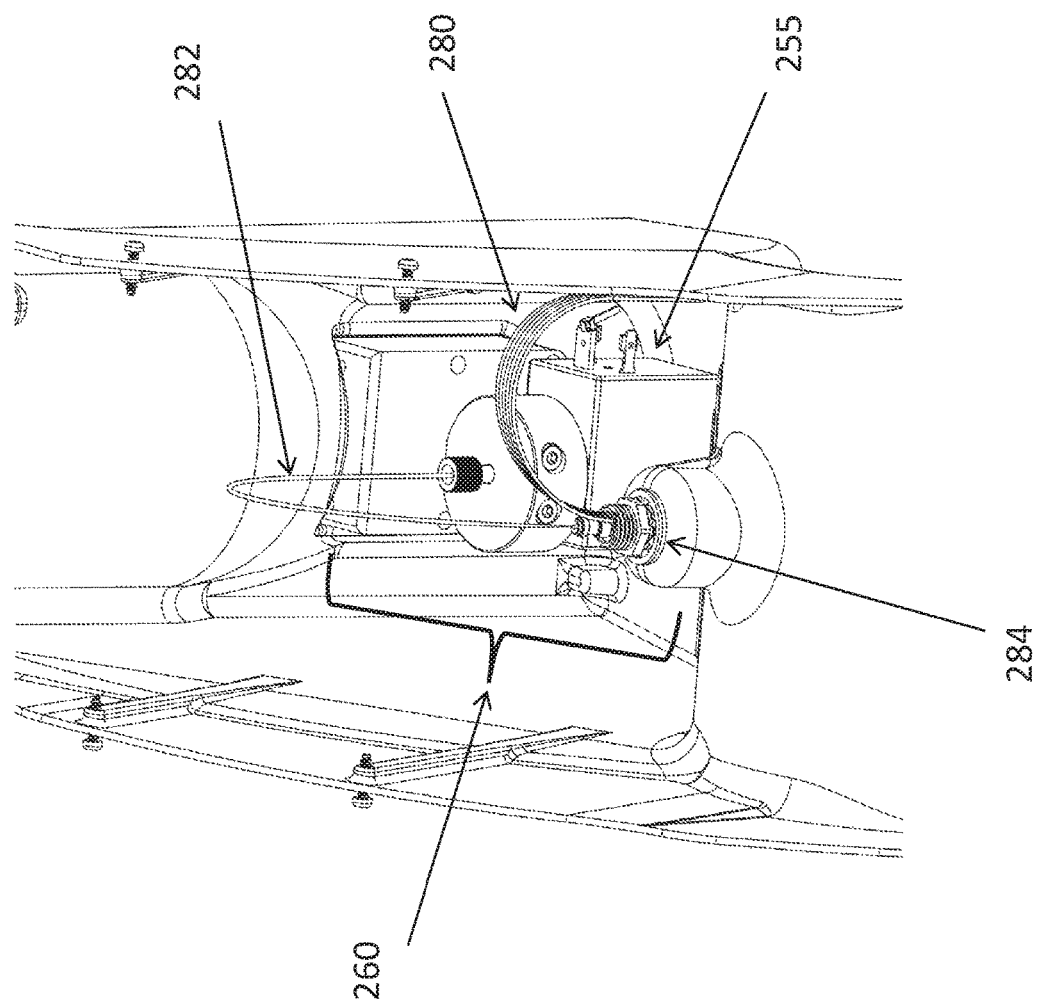
FIG. 2 shows an enlarged front view of the portable electro-mechanical cryosurgical system of FIG. 1A with the control panel removed showing the interior of the system.

As shown in FIGS. 1A and 1B, the system 100 includes a portable countertop enclosure 128 and a wand 104. FIG. 2 shows an internal portion of the portable countertop enclosure 128 with the control panel 124 removed. Portable countertop enclosure 128 houses a cryogen supply (shown in FIG. 8A, for example), system electronics 255, flow path assembly 260 (shown in detail in FIGS. 8A-8C), and wand wiring 280. Cryogen flow tube 282 extends from the flow path assembly 260 through the wand mount 284 and out to the wand 104.

System Housing and Control Buttons and Electronics

The invention includes many features that ensure its ease of use and facilitate human factors. As shown in FIG. 1A, the control panel 124 faces front and is angled up and slightly back for easy user interaction. In this configuration, a clinician can easily see all indicators and controls from standing and sitting positions. Four buttons 108, 112, 116, 120 control the system functions. Standby actuator 116 activates the system 100 and serves as an on/off switch. Treatment time selector 112 sets the treatment time interval while the wand light actuator 108 turns on an illumination source on the tip of the wand 104 to illuminate the treatment area. Reset actuator 120 interrupts a treatment and returns the system 100 to a standby state. The actuators can be buttons, switches, relays, and other devices for making and breaking a connection in an electrical circuit.

The control panel 124 also includes a cryogen source level indicator 132 that provides an indication to the user of how much cryogenic material remains in the system. FIG. 1A shows cryogen source level indicator 132 as an LED bar on the control panel 124 in an example configuration, but the source level indicator 132 can include other types of level gauges indicate to the user the amount of cryogenic material available for use. The level indicator provides an indication of the amount of cryogenic material remaining in the cryogen tank. When a new tank is installed, the cryogen source level indicator 132 is reset to "full." As treatments are performed, the switch PCB (reference numeral 1030 in FIG. 10) tracks the number of treatments and the duration of each treatment. The input PCB 1010 calculates the amount of cryogenic material used in those treatments based on number and duration and subtracts it from the "full" level. The system 100 provides a visual indication of the amount of cryogen remaining in the cryogen tank by illuminating cryogen source level indicator 132 on control panel 124.

Figure 3:
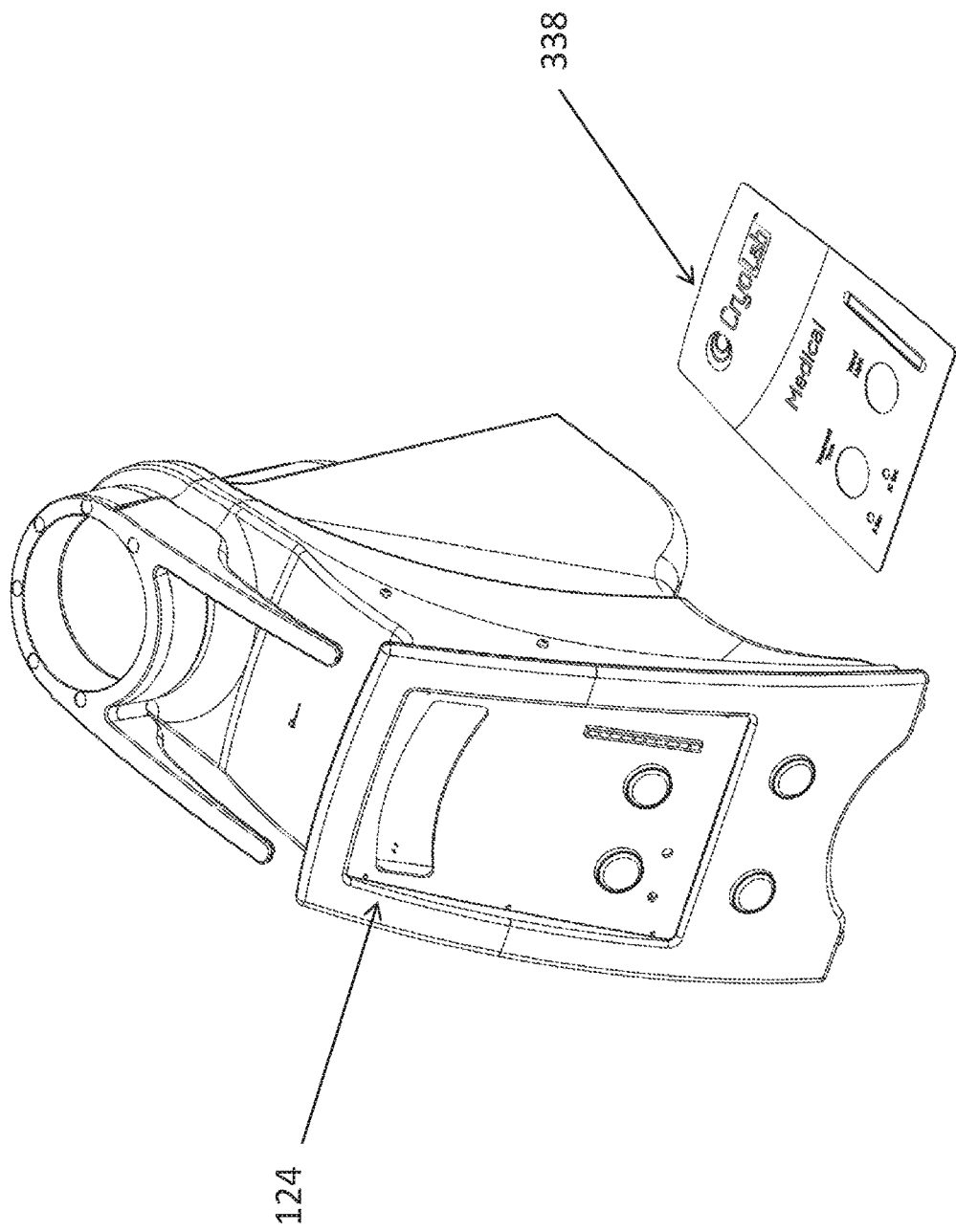
FIG. 3 shows a front perspective view of a portable electro-mechanical cryosurgical system in accordance with the invention with the control panel faceplate removed.
Figure 4:
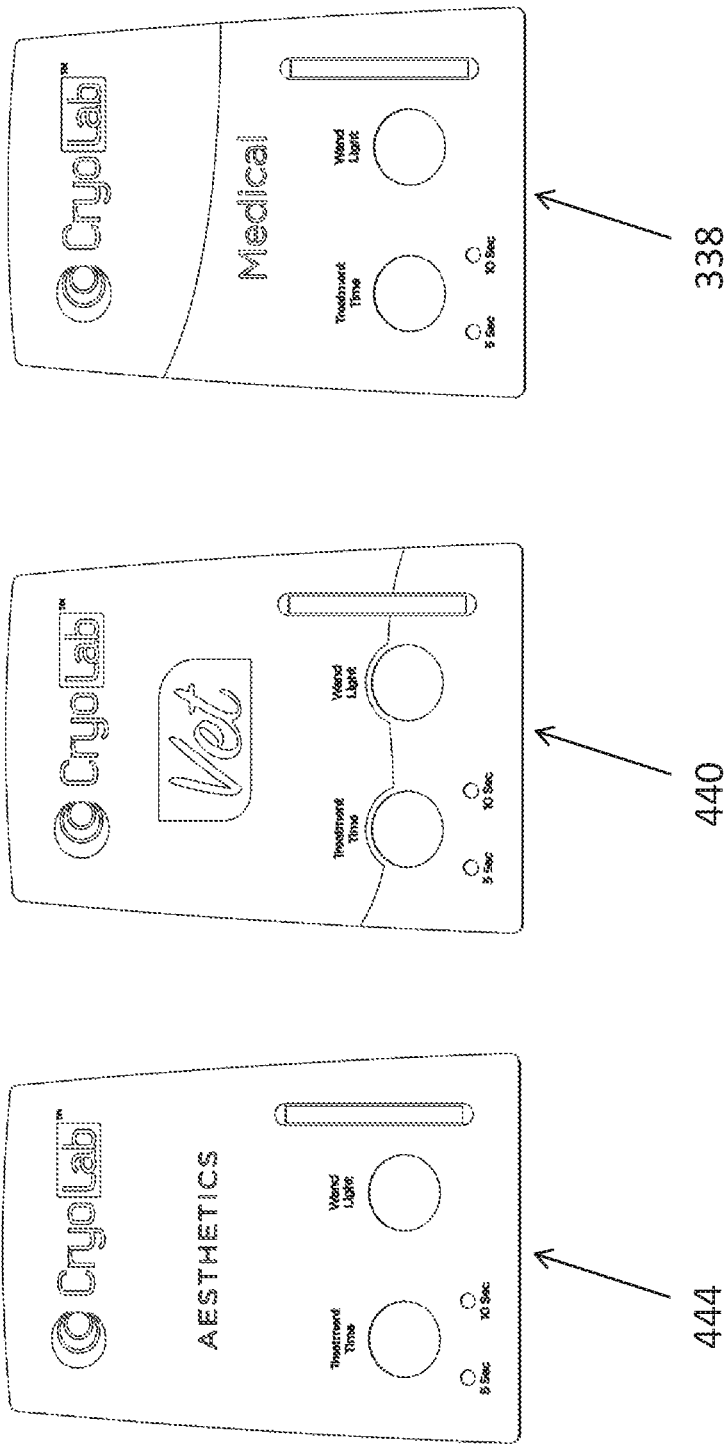
FIG. 4 shows a number of example faceplates to attach to a control panel of a portable electro-mechanical cryosurgical system in accordance with the invention.
Figure 5:
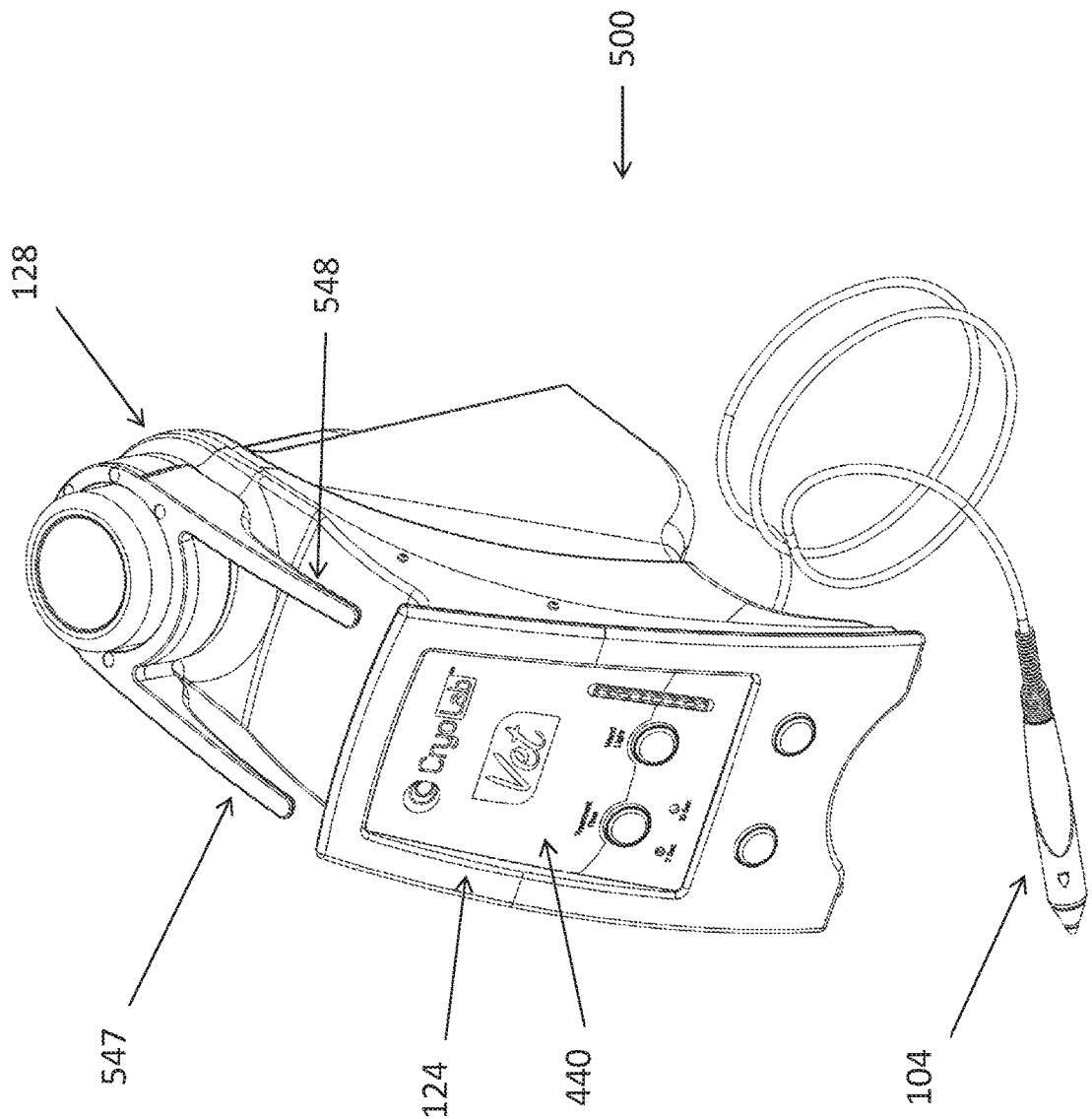
FIG. 5 shows an example portable electro-mechanical cryosurgical system configured for veterinary use.

As shown in FIG. 3, the system 100 includes a faceplate 338. Clinicians can use the invention in a number of different treatment environments, including medical treatments, veterinary treatments, and aesthetic treatments. Aesthetic treatments can include superficially or deeply freezing unwanted topical lesions as well as delivering cold gases to stimulate localized circulation and increase localized oxygenation. Different system configurations provide different options, depending upon the treatment environment. For example, treatment times in the medical environment differ from treatment times in the aesthetic environment. Veterinary treatments may incorporate different cryogenic materials than aesthetic treatments. The system 100 is configured for the desired environment, and the example faceplates shown in FIG. 4 provide an indication of the system configuration with aesthetic faceplate 444, veterinary faceplate 440, and medical faceplate 338. FIG. 5 shows an assembled veterinary system 500 with control panel 124 and veterinary faceplate 440.

Figure 10:
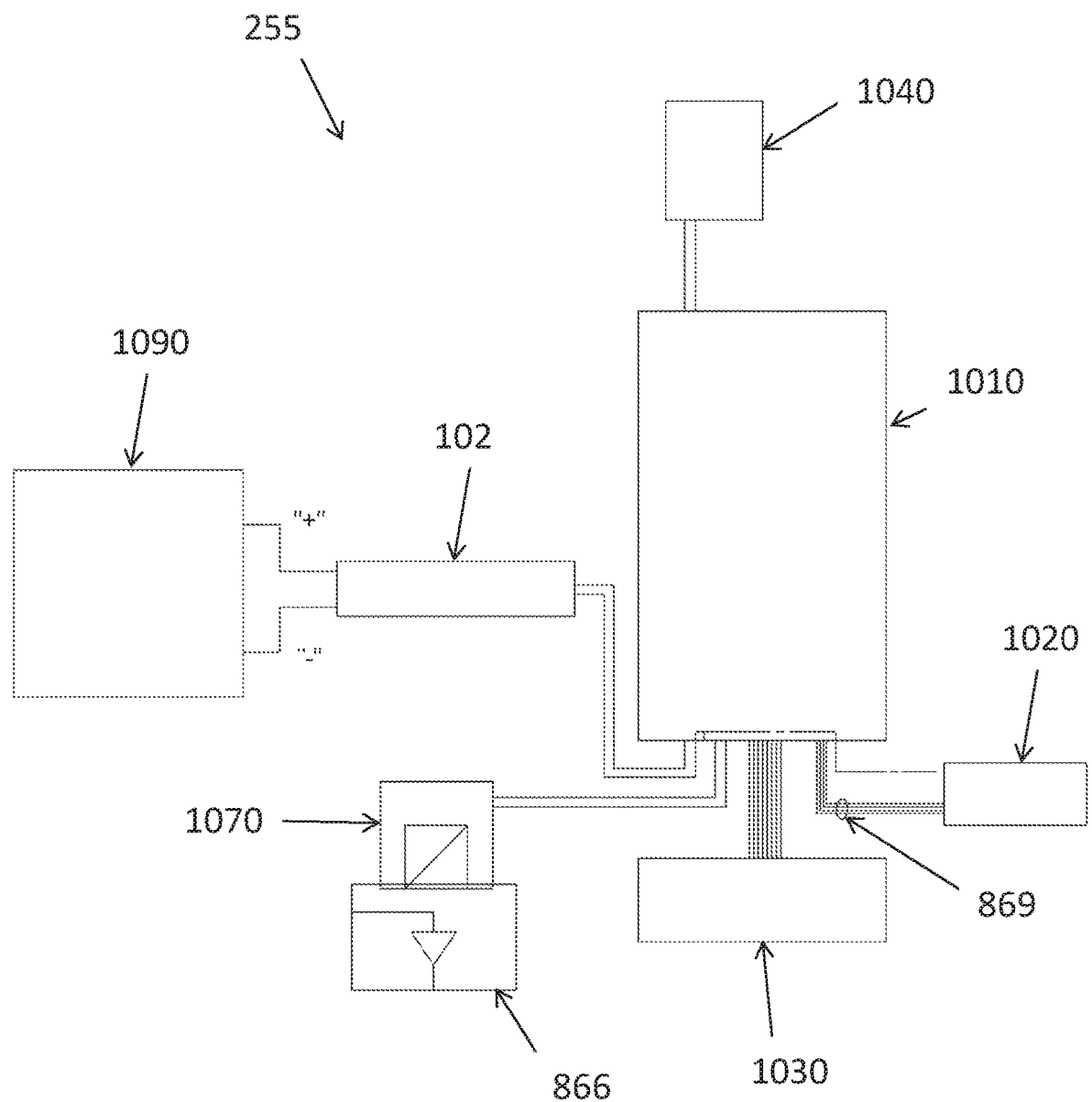
FIG. 10 shows an example implementation of the system electronics of the invention.

FIG. 10 shows a diagram of an example configuration of the system electronics 255 of the invention. System electronics 255 includes an input PCB 1010 connected to wand PCB 1020 via wand cable 869. Switch PCB 1030 provides connections between the input PCB 1010 and user interface switches (standby actuator 116 and reset actuator 120 shown in FIG. 1A). Input PCB 1010 provides power and logic to energize solenoid coil 1070 to open and close solenoid valve 866. System electronics 255 are powered by power supply 1090 via power entry connector 102. Power supply 1090 can be a battery power supply or an AC power supply regulated to provide suitable power to input PCB 1010 and the other system electronics. A battery 1040 provides power to the memory circuits when the system electronics is not fully powered.

Cryo Spray Application Wand

Clinicians and other users provide cryogenic material to patient treatment areas using wand 104 shown in FIGS. 1A, 1B, and 5. Also, FIGS. 6 and 7 show example wands 104, 604. The wands 104, 604 fit ambidextrously and comfortably into a user's hand and, because the invention includes a closed gas flow architecture, the wands are omni-directional, allowing clinicians to treat lesions in any direction or orientation. As shown in FIG. 7, treatment activation button 711 is positioned on the wand 104 so it can be activated with a light force from either the user's index finger or thumb. As shown in FIG. 6, the wand 104 includes an illumination source 606, such as an LED light for example, for extra illumination of the treatment area if the user chooses. To select the wand illumination source 606, the user selects wand light actuator 108 on the control panel 124 as shown in FIG. 1A.

System Portability

As shown in FIG. 1A, a user can carry the system 100 of the invention by one or both of the handles 147, 148 located at the top of the portable countertop enclosure 128. The design and manufacture of the system, including the center of mass of the enclosure 128, ensures that the unit swings minimally and hangs as expected under the handles 147, 148 when a user lifts the unit. As shown in FIG. 1B, the enclosure 128 includes feet 153, 154, 155, 156 positioned under the enclosure to assure stability and prevent sliding when the system is in operation.

System Power Supply

An external, low voltage power supply (reference numeral 1090 shown in FIG. 10) provides power to the system 100. As shown in FIGS. 1B and 10, a power jack 102 is located on the back of the system (rear of enclosure 128). In one example configuration, the power supplied by the external supply also maintains an internal battery (shown as reference numeral 1040 in FIG. 10) for electronics memory (not shown separately) which keeps track of cryogen usage via cryogen source level indicator 132. In one example configuration, the entire system is powered by an external battery providing additional portability and ease of use.

System Internal Features (Including Cryogen Gas Supply and Flow Path)

Figure 8A:
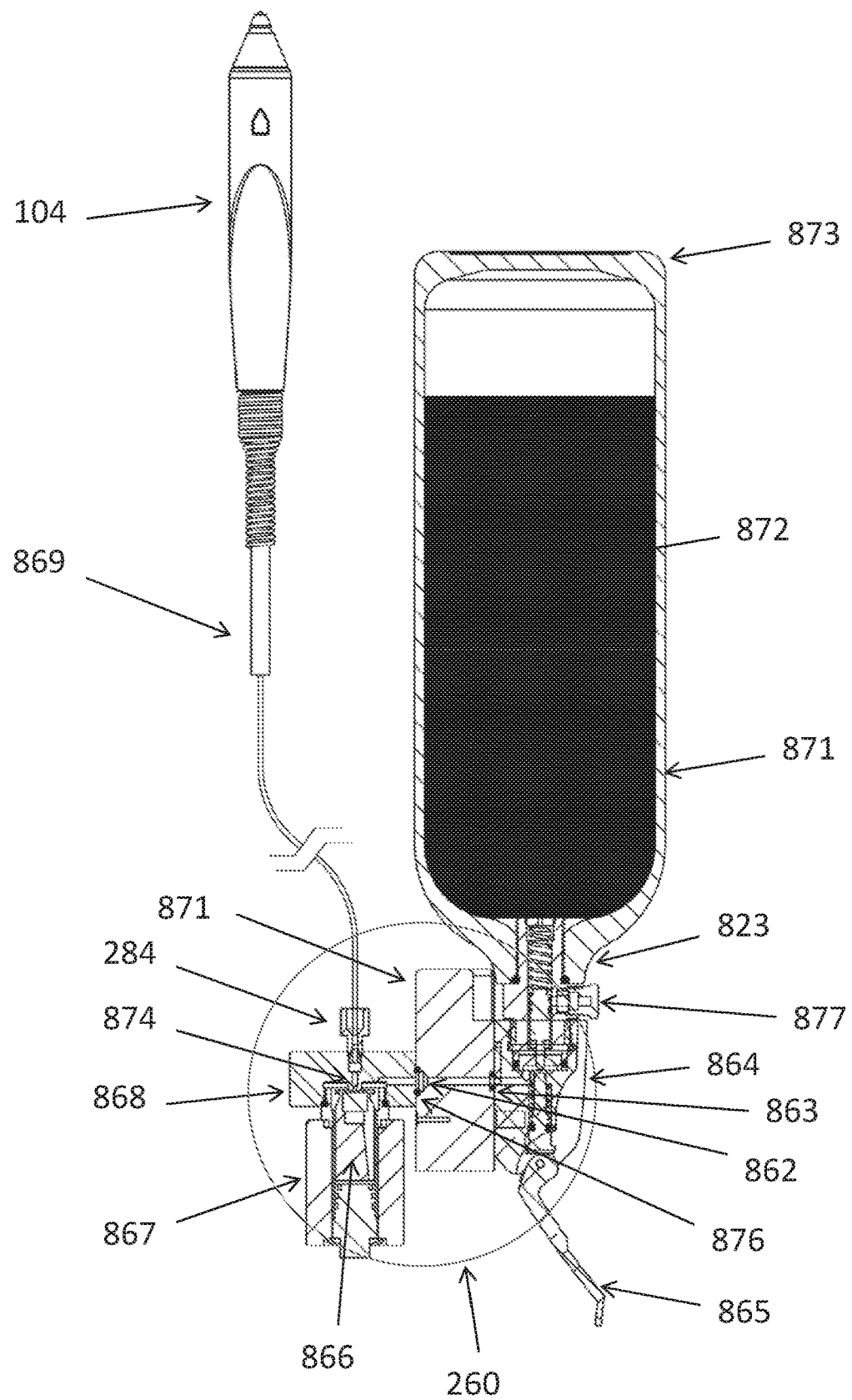
FIG. 8A shows an internal view of a cryogen flow path assembly in accordance with the invention.
Figure 8B:
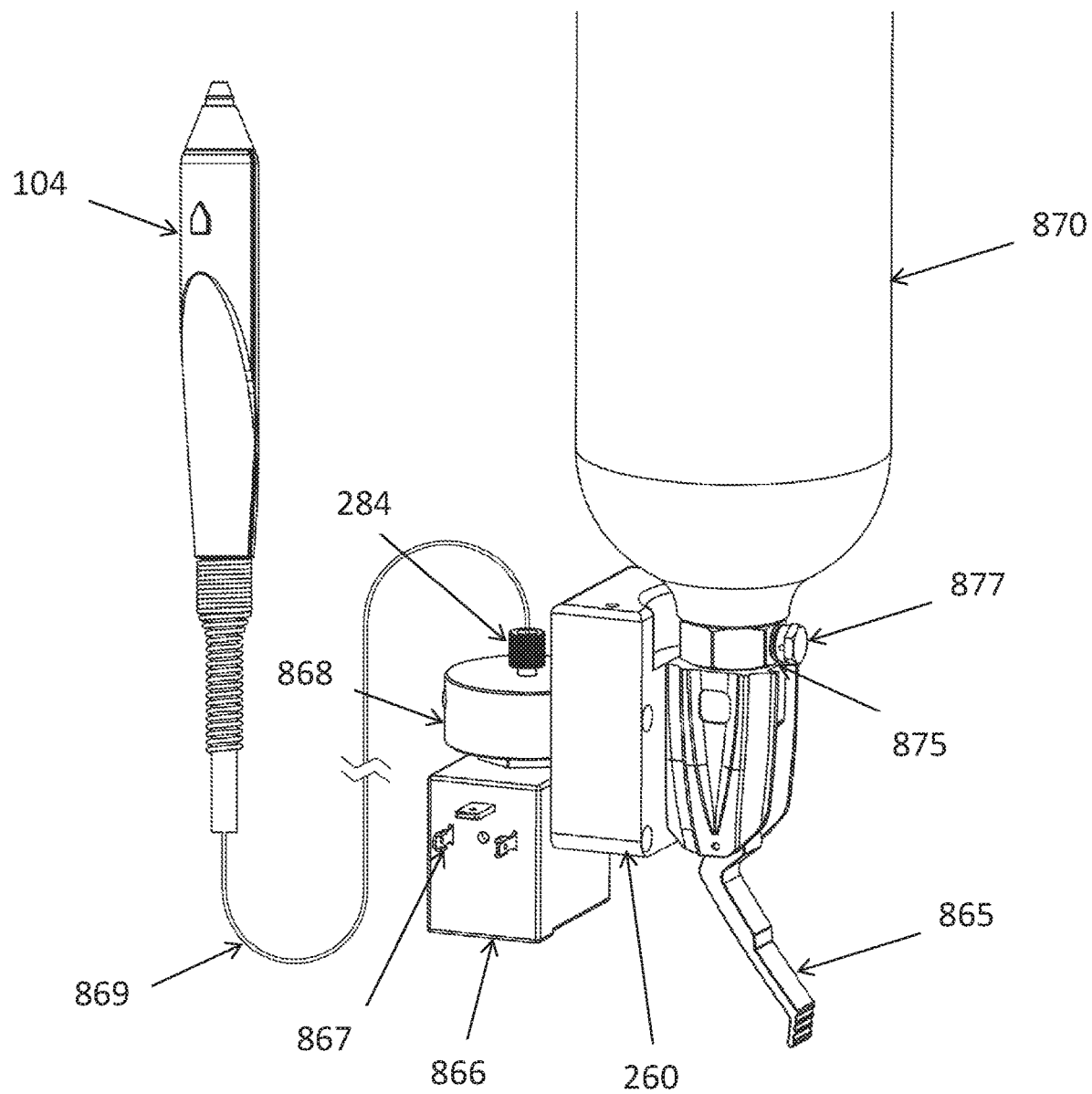
FIGS. 8B-8C show additional views of a cryogen flow path assembly in accordance with the invention.
Figure 8C:
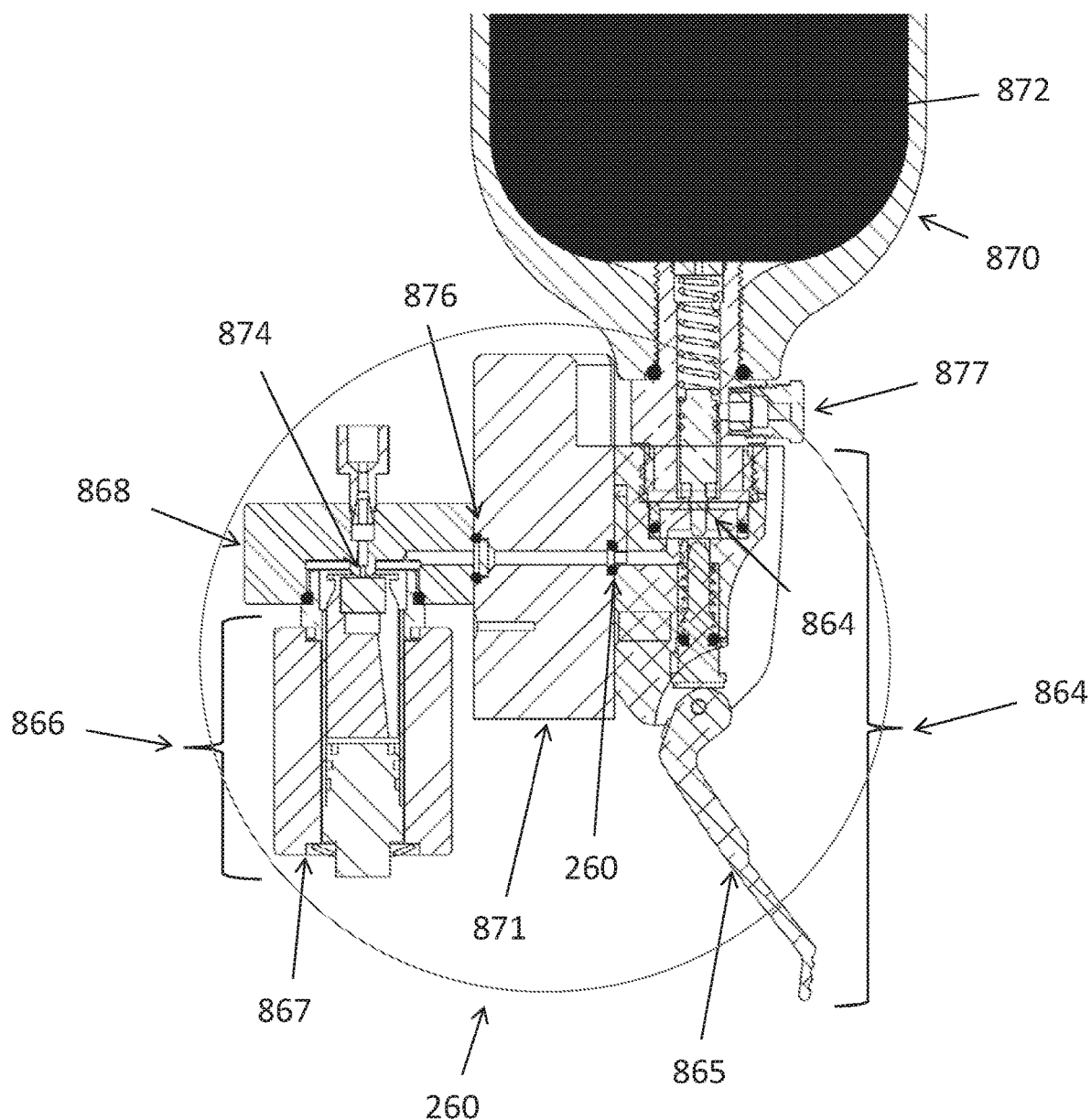

Internal to the portable countertop enclosure 128, the system 100 includes a cryogen source and a specially developed flow control path. FIGS. 8A-8C show flow path assembly 260 along with other internal and external system components with the portable countertop enclosure 128 removed.

The cryogen tank 870 has been developed to be durable, convenient to use, shippable, and provides an interface that is manufactured in high volume and for proven reliability. The cryogen tank 870 stores a volume of cryogen (cryogenic material 872, for example) during shipping and storage. The cryogen tank 870 is housed inside the rear of the portable countertop enclosure 128 and connects to the flow control path (such as flow path assembly 260, for example) through a pin valve (not shown separately), installed in the cryogen tank 870, that seals the cryogen tank 870 during shipping and storage. The quick-change high pressure cylinder adapter 864 engages and opens the pin valve in the cryogen tank 870 when lever 865 is actuated. The quick-change high pressure cylinder adapter 864 works in tandem with burst disk 877 on the pin valve assembly 875 of the cryogen tank 870 that controls overpressure, providing additional safety measures. Cryogen tank 870 interfaces with a main cryogen supply valve via a thread and O-ring combination (not shown separately). When installed in the enclosure 128, the top of the tank 870 protrudes only minimally above the handles 147, 148 of the system enclosure 128 to both mechanically protect the tank 870 and to limit the torque a user can apply when threading the tank 870 to the main cryogen supply valve. A large lever 865 is part of the flow path assembly 260 and engages at the neck 823 of the tank 870 to deliver the cryogen (cryogenic materials 872) to the rest of the flow path assembly 260. When activated, the lever 865 opens the pin valve in the cryogen tank 870. A flow block 871 supports the components of the flow path (assembly) 260 and includes O-ring seals 863, 876 for the components.

As shown further in FIGS. 8A-8C, the cryogen tank 870 interfaces and seals to an adapter 864. As outlined above, adapter 864 is a quick change, high-pressure cylinder interface with a pressure relief port for easy installation when changing the cryogen cylinder (tank 870). A user does not need any special tools to exchange cryogen cylinders. The mating threads of the cryogen tank pin valve thread with the mating threads of the adapter 864, and the combination assembly can be quickly changed out when the cryogen is depleted. The adapter 864 includes a post in a base. As a user screws the adapter 864 into the cryogen tank 870, the pressure from the cryogen tank pushes the post to a closed (sealed) position in the adapter 864 that prevents cryogen gas and/or cryogen liquid from flowing out of the adapter. When the user installs the combination of the cryogen tank 870 and adapter 864 into the flow path assembly 260, the lever 865 receives the adapter 864 and pushes on the post, which depresses the pin valve 875 in the cryogen tank 870 enabling the cryogen 872 to flow into the flow path assembly 260. Solenoid valve 866 is normally closed, which prevents the cryogen from dispensing until the clinician initiates treatment.

To open the cryogen tank 870 to allow the flow of cryogenic material 872 through the flow path assembly 260, an operator engages lever 865, which in turn pushes a post in the pin valve assembly that opens the cryogen tank pin valve.

Once a user engages the lever 865, the cryogenic material 872 from the cryogen tank 870 begins to flow through flow path assembly 260. In-line filter 862 blocks any foreign material from entering the remaining flow path while allowing the cryogenic material 872 to flow freely.

After the system filters the cryogenic material 872 and assures that the pressure of the cryogenic material 872 is within acceptable limits, the cryogenic material 872 continues through the flow path assembly 260 to the solenoid valve 866. The specifically designed high pressure electromechanical solenoid valve 866 provides treatment time control. The solenoid valve 866 handles (receives) the high-pressure cryogenic materials in the flow path and allows placement of the cryogen flow tube 282 very close to the solenoid valve seat 874. This close placement of the cryogen flow tube 282 to the valve seat 874 provides an improved response time as measured from the time the user activates the treatment activation button 711 and the time the system delivers the cryogenic material to the treatment area. Previous systems included solenoid valves that did not provide the operating pressure and flow rate characteristics of the solenoid valves of the invention. The solenoid valves of the invention include improved valve seat and valve base geometries to provide substantially a zero dead volume, leading to improved response times. In some example implementations of the invention, the response time from activation of the treatment button to delivery of the cryogen to the treatment area is less than two (2) seconds. Previous systems and cryogenic valves had a much slower response times, which resulted in inaccurate patient treatment times.

The system electronics 255 housed in the portable countertop enclosure 128 triggers the solenoid valve 866 to allow cryogenic material 872 to flow for a predetermined time. For example, during manufacture, the system electronics 255 can be configured to provide and deliver two different treatment times. That is the amount of time that the cryogen will be delivered to the patient treatment area each time the treatment activation button 711 on the wand 104 is pushed. In one example configuration, the first treatment time is set to a five (5) second treatment of cryogenic material to the patient treatment area. Similarly, a second treatment time of delivery of cryogenic material to the patient treatment area can be configured, such as ten (10) seconds. Users can determine and program treatment times based on the clinical environment and patient needs.

Configuring the system electronics (using dip switches, integrated circuits, RC networks, oscillators, and other timing circuitry) for the predetermined times opens the solenoid valve 866 for that predetermined time when the clinician activates the treatment activation button 711 on the wand 104 (shown in FIG. 7). The solenoid valve 866 operates consistently and effectively at the pressures exerted by the cryogenic material 872. The valve seal (not shown separately) is designed and manufactured to avoid swelling and failure when exposed to the cryogen. That is, the valve seal maintains its original geometry when exposed to compatible cryogens. While components of any valve (body, bonnet, stem, stem seals, ball, seats, etc.) will contract and expand at different rates because of different material composition or the amount of time exposed to the cryogenic material, the solenoid valve 866 provides a positive cryogenic seal that inhibits cryogenic material flow when the valve 866 is shut. The solenoid valve 866 interfaces with the flow block 871 via a solenoid valve base 868.

The solenoid valve base 868 holds the solenoid valve 866 and forms the seat against which the valve 866 seals. The valve base 868 was designed and manufactured to minimize the seal area to allow high-pressure operation. Also, the "dead volume" (the volume between the flow restrictor (i.e., the point where the flow path assembly 260 transitions to the cryogen flow tube 282) and the valve seat 874) of the valve 866 was minimized in the device as described above, as the solenoid valve 866 and cryogen flow tube 282 are in close proximity. The low dead volume of the valve 866 translates to a rapid flow response when the user actuates the treatment activation button 711 on the wand 104 and delivers the cryogenic material 872 to the treatment area.

Once the cryogenic material 872 flows through the solenoid valve 866, the cryogenic material 872 moves through the wand mount 284 and leaves the portable countertop enclosure 128 of the system 100 traveling toward the wand 104. The cryogenic material 872 flows through wand cable 869 via cryogen flow tube 282.

Figure 9:
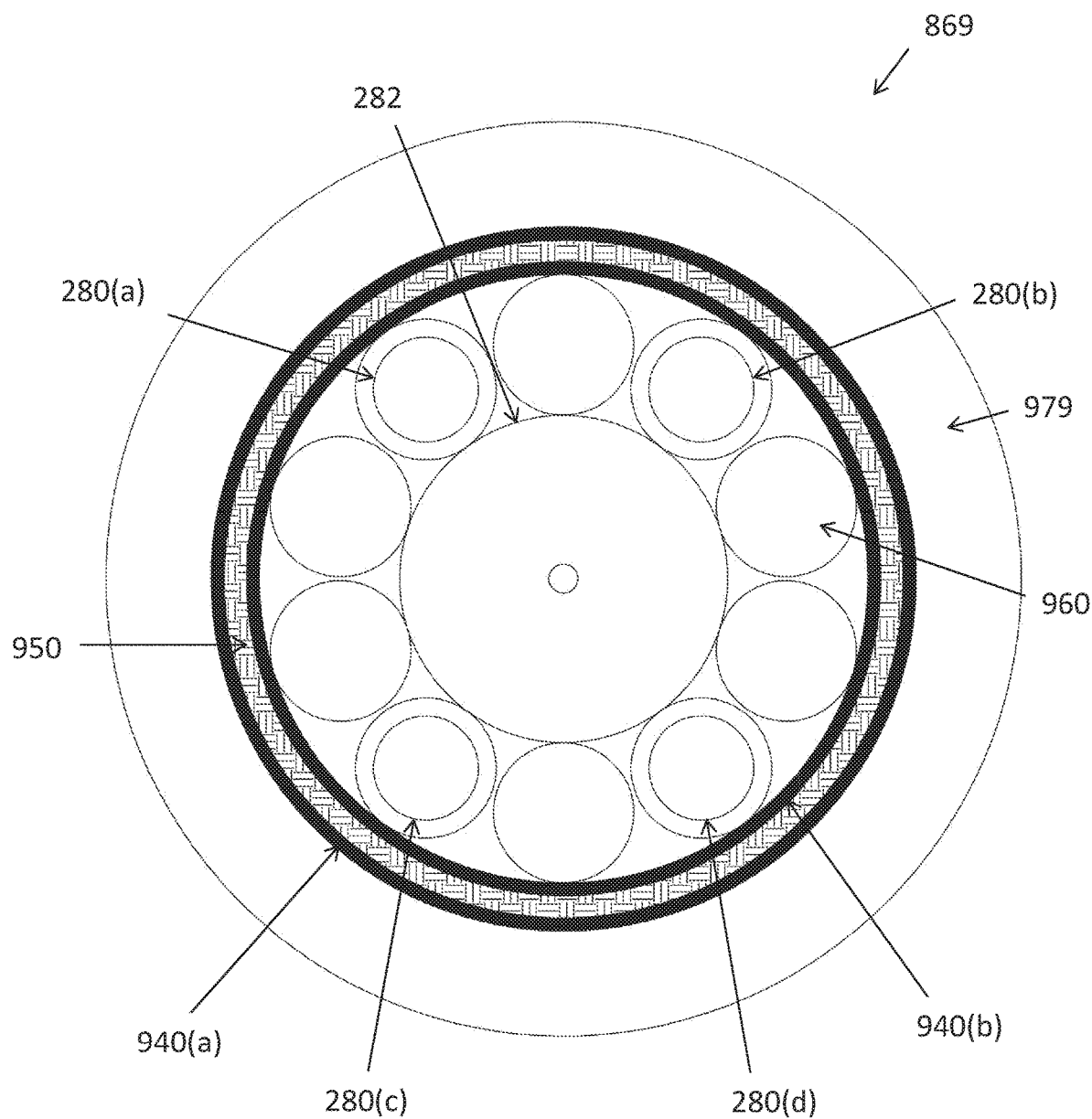
FIG. 9 shows a cross-sectional view of an example wand cable for use in a portable electro-mechanical cryosurgical system of the invention.

As shown in FIG. 9, wand cable 869 includes cryogen flow tube 282 that is a conduit for transporting cryogenic material 872 from the flow path assembly 286 to the wand and as a conduit for electrical wiring 280 used in concert with the treatment activation button 711 (shown in FIG. 7, for example). As shown in FIG. 9, in one example implementation of the invention, wand cable 869 includes the cryogen flow tube 282 at the central axis of the wand cable 869. Arranged about the circumference of the cryogen flow tube 282 are wand wiring cables 280(a), 280(b), 280(c), and 280(d), which provide power and logic to the wand 104 from the system electronics 255 in the internal portion of the portable countertop enclosure 128. Filler material 960, such as fiberglass fillers, for example, can be used to provide additional rigidity and stability to the wand cable 869. A deformable filler with lubricating properties 940(b) can serve as a covering of the outer circumference of the wand wiring 280 and fillers 960. For example, PTFE tape can be used as a covering 940(b) of the wand wiring 280 and fillers 960. A braided shield 950 can protect the wand wiring cables 280 and can also provide an electronic ground point for the cables 280. Another layer of deformable filler with lubricating properties 940(a), for example, PTFE tape, can cover the outer circumference of the braided shield 950. A wand cable jacket 979 provides protection for the internal components of the wand cable 869.

Cryogen flow tube 282 (inside wand cable 869) restricts and controls the flow of the cryogenic material 872 so that the system 100 delivers the correct cryogenic material dose to the patient treatment area. In contrast to previously-available systems with dispensing devices which are limited by having to point downward in order to assure liquid cryogen flow, the cryogen flow tube 282 and wand cable 869 allows the omni-directional delivery of the cryogenic material to the treatment area and allows the user to apply cryogenic material in any direction while continually supplying liquid cryogen to the restrictor inlet in the wand mount 284 (i.e., the transition point from the flow path assembly to the cryogen flow tube 282).

Flow Control Wand Cable Engineering

A critical design feature of cryogen delivery devices is their ability to meter the flow of high-pressure cryogenic gases that are discharged from the unit. Previous devices primarily controlled the flow of the cryogenic gases by employing large metal valves and regulators to control and dispense liquid cryogens through a (typically) small orifice. The claimed invention controls the flow of the cryogenic materials using the physical dimensions of the flow restrictor tube (cryogen flow tube 282).

The invention incorporates a cryogen flow tube 282 designed and manufactured to provide flow rates comparable to existing systems while eliminating cumbersome and problematic valving mechanisms. For example, the invention uses tubing (i.e., cryogen flow tube 282) from the flow block 871 to the tip of the wand 104 to dispense cryogen. Early in development, it was initially thought that the capillary flow equation shown below would govern the design and dimensions of the tubing. Specifically, $$\Delta P = \frac{8 \mu L Q}{\Pi r^4}$$

where $\Delta P$ is the pressure difference between the two ends of the cryogen flow tube, L is the length of the cryogen flow tube, $\mu$ is the dynamic viscosity of the cryogenic material to be delivered, Q is the volumetric flow rate of the cryogenic material, and r is the radius of the cryogen flow tube.

Delta P is known from the bottle pressure of the cryogen. For $CO_2$ it is 830 psi (5720 kPA). For $N_2O$ it is 730 psi (5053 kPa). The pressure drop is to nominally atmosphere (0 pressure) along the length of the cryogen flow tube.

In using this capillary flow equation, the dynamic viscosity of the cryogen is difficult to measure and quantify, so measurements of flow rates through relatively short tubing lengths were used to determine the expected flow rate through longer tubing.

Since $\mu$ (dynamic viscosity) is difficult to measure, llaboratory comparisons were used to make the cryogen flow tube length determinations. A measured experiment determined that 95 mm of 0.003" Ø tubing (that is, 0.076 mm Ø, which is 0.038 mm radius) provided the desired flow rate of the cryogen. To determine the necessary length, L, of cryogen flow tube for 0.007" Ø tubing (that is, 0.1778 mm Ø, which is 0.0889 mm radius), the capillary flow equation provided:

$$\Delta P = \frac{8 \mu L Q}{\Pi r^4}$$

To determine the length of the 0.007" Ø tubing, the capillary flow equation dictated:

Tubing 1($r_1$ = 0.038 mm, $L_1$ = 95 mm)

$$\Delta P = \frac{8 \mu L_1 Q}{\Pi r_1^4}$$

$$\frac{\Delta P \Pi}{8 \mu Q} = \frac{L_1}{r_1^4}$$

Tubing 2($r_2$ = 0.0889 mm, $L_2$ = to be determined)

$$\Delta P = \frac{8 \mu L_2 Q}{\Pi r_2^4}$$

$$\frac{\Delta P \Pi}{8 \mu Q} = \frac{L_2}{r_2^4}$$

Using measurements of various lengths of tubing, the viscosity, $\mu$, was eliminated as a variable in the capillary flow equation by using the ratio of the known flow for short tubing to a longer length/different diameter tubing. Since $\Delta P$, $\mu$, and Q are all constant for the system, the capillary flow equation relationships reduce to:

$$\frac{L_1}{r_1^4} = \frac{L_2}{r_2^4}$$

Solving for L2, the unknown length of 0.007" Ø tubing, the capillary flow equation dictated:

$$L_2 = \frac{L_1 r_2^4}{r_1^4}$$

Using the actual measurements provided:

$$L_2 = \frac{(95 \text{ mm})(0.0889)^4}{(0.0381)^4}$$

$$L_2 = 2815 \text{ mm}$$

$$L_2 = 2.8 \text{ m}$$

Using the capillary flow equation, unexpectedly, the length of the tube is predicted to be much longer than experiments show is necessary. Specifically, the calculation predicted that a 0.007" ID tube would need to be 2.8 m long to provide the target dispense rate.

However, actual experiments showed that a tubing length of only 1.5 m is the correct length to match the target flow rate. Additionally, different tubing materials and outside diameters also impacted the quality of a $CO_2$ "ice" dispersion. The choice of cryogen flow tube materials affected performance of the solenoid seal when switching between different cryogenic materials. For example, polytetrafluoroethylene (PTFE) worked well in delivering cryogenic material, but did not provide an optimal seal.

When the correct tubing material, length, and ID are chosen, the flow rate of CO2 is correct, and $CO_2$ ice is dispensed as expected. Conversely for example, if non-polymeric tubing is used, no ice sprays at all, and only $CO_2$ gas exits the cryogen flow tube. These discoveries lead to a conclusion that a phase transformation of the cryogen is taking place at some distance along the tubing flow path. This phase transformation from the liquid cryogen to a solid, in the case of $CO_2$, is the reason that the experimental flow rates diverge from the theoretical flow rates. When the length of tubing is too long (such as when using the calculated and/or expected lengths of tubing), no ice sprays at all, and only cryogenic gas exits the cryogen flow tube. The cryogenic materials appear to gain heat as they flow along the greater length of tubing. Additionally, when the length of the cryogen flow tube is too short, the dose of cryogenic material delivered to the patient is too high—the system blasts ice onto the affected area. The ratio of the inner diameter of the cryogen flow tube to the length helps maintain the liquid state of the delivered cryogenic material.

The system of the invention incorporates the unexpected experimental observations to meet the design and performance targets for the system while ensuring ease of operation. The predicted flow path for the tubing would have been much longer and cumbersome for a practitioner to operate.

System Set Up

The invention provides improvements in operation over existing cryosurgery systems in both usability of the device and reliability of the system. For example, the portable countertop enclosure 128, wand cable 869, and wand 104 ship separated from cryogen tank 870. When setting up and configuring the system 100, the user places the cryogen tank 870 in the rear of the portable countertop enclosure 128. The user threads the cryogen tank 870 (including pin valve assembly 875) into place until its rotation stops. An external O-ring on the pin valve assembly 875 seals the tank 870, so the cryogen tank 870 properly seats with only a very light torque. Once the cryogen tank 870 is in place, the user lifts up the lever 865 to activate the adapter 864 to enable the flow of cryogenic material.

The lever 865 action opens the cryogen tank pin valve (not shown separately) and pressurizes the cryogen flow path in the flow path assembly 260. The user then connects the system power supply (not shown separately). Once power is applied to the system, the user resets the cryogen source level indicator 132 to full, indicating installation of a new cryogen tank 870. For example, in one example configuration of the invention, the user operates a small magnet, shipped with the cryogen tank 870, to set the cryogen source level indicator 132 to "full." As the system 100 is used to perform cryosurgical procedures and to treat affected patient areas, an internal memory tracks the usage of the cryogenic material 872 and shows an approximate amount of cryogenic material 872 remaining in the cryogen tank 870. Finally, the user follows the treatment instructions (outlined below) to execute a single treatment, such as a ten (10) second treatment, which primes the components along the cryogen flow path. Once primed, the initial system set up is complete.

Cryogenic Treatments

When the user is ready to begin a treatment, the user connects the system 100 to external power supply (not shown separately). The user presses the standby button (actuator 116) to activate the system 100. The user presses the treatment time button (selector 112) to select the desired treatment time. When the user presses the treatment time selector 112, the treatment time cycles through two pre-determined and pre-configured treatment time options. In one example configuration of the invention, the two treatment times are 5 seconds and 10 seconds. So when the user presses the treatment time selector 112, the treatment time cycles from 0 seconds to 5 seconds. When the user presses the treatment time selector 112 again, the treatment time cycles from 5 to 10 seconds. When the treatment time is zero seconds, both treatment time 1 indicator 113 and treatment time 2 indicator 114 are off. When the treatment time cycles to 5 seconds (i.e., the first pre-determined and pre-configured treatment time), treatment time 1 indicator 113 illuminates. When the treatment time cycles to 10 seconds (i.e., the second pre-determined and pre-configured treatment time), treatment time 2 indicator 114 illuminates. As indicated above, the treatment times can be configured using the system electronics 255 (e.g., timing circuits, DIP switches, RC networks, etc.)

Additionally, the user can choose to illuminate the treatment area at any time by selecting the wand light actuator 108. Once the user selects the desired treatment time and illuminates the treatment area, if desired, the user positions the wand 104 for treatment of the affected patient area and presses the treatment activation button 711 on the wand 104. This selection initiates the treatment, allowing the cryogenic material to spray. Once the user presses the treatment activation button 711 on the wand 104, the system 100 will deliver the cryogenic material 872 to the treatment area for the full treatment time, whether or not the user holds the treatment activation button 711 the entire treatment time. This allows the user to change position of the wand 104 as necessary to complete an effective treatment of the patient area.

Once the cryogenic material application completes (i.e., the system has delivered the cryogenic material for the full selected treatment time), the user must re-press the treatment activation button 711 on the wand 104 to initiate another delivery of the cryogenic material. Each time the user presses the treatment activation button 711 to start the cryogenic material delivery, the user will need to re-press the button 711 to initiate another spray. If the user wishes to terminate a treatment, the user presses the Reset button (actuator 120). The reset actuator 120 places the system 100 back into the standby mode, stopping any initiated treatment in the process.

The invention addresses design and ease of use difficulties of many previously available cryosurgical systems. The invention provides an economical and easy to use platform when performing a large number of cryo-treatments.

We claim:

1. A portable cryosurgical device for directly delivering a cryogen to a target treatment area, the device comprising:
   a cryogen flow tube connected in fluid communication with a cryogen source via a flow path assembly;
   the flow path assembly positioned between the cryogen source and the cryogen flow tube, wherein the flow path assembly includes:
      a valve positioned between the cryogen source and the cryogen flow tube and in fluid communication with the cryogen source and the cryogen flow tube, wherein the valve includes:
         a valve seat at a terminal end of the valve and including an inlet side and an outlet side, wherein the
         inlet side of the valve seat receives the cryogen from the cryogen source; and
         the outlet side of the valve seat receives the cryogen from the inlet side of the valve seat when the valve seat moves from a closed position to an open position;
      an actuator movable to cause the valve seat to move from the closed position preventing passage of the cryogen from the inlet side of the valve seat to the outlet side of the valve seat to the open position permitting passage of the cryogen from the inlet side of the valve seat to the outlet side of the valve seat;
   wherein the inlet side of the valve seat and the outlet side of the valve seat are positioned in fluid communication with the cryogen flow tube to produce a dead volume of less than 25 μL and to provide substantially instantaneous delivery of the cryogen to the target treatment area upon actuation of the device.

2. A portable cryosurgical device of claim 1, wherein a volume of cryogen directly delivered to the target treatment area is substantially instantaneously delivered and is metered based on a predetermined dispense time commencing upon activation of the device.

3. A portable cryosurgical device of claim 2, wherein the volume of cryogen delivered is further metered based on a flow rate through the cryogen flow tube.

4. A portable cryosurgical device of claim 3, wherein the flow rate through the cryogen flow tube is based on at least one of length of the cryogen flow tube and inside diameter of the cryogen flow tube.

5. A portable cryosurgical device of claim 2, wherein the portable cryosurgical device further comprises a portable countertop enclosure that houses the cryogen source, and wherein the portable countertop enclosure includes a treatment time selector and the predetermined dispense time is at least one second.

6. A portable cryosurgical device of claim 1 further comprising:
   a dispensing wand that receives and houses the cryogen flow tube.

7. A portable cryosurgical device of claim 6, wherein the dispensing wand is omni-directional and substantially instantaneously delivers the cryogen from a wand tip independent of the orientation of the dispensing wand in relation to the target treatment area.

8. A portable cryosurgical device of claim 7, wherein the dispensing wand delivers a liquid cryogen from the wand tip.

9. A portable cryosurgical device of claim 1, wherein the cryogen source is a single refillable cylinder.

10. A portable cryosurgical device of claim 1, wherein the flow path assembly includes:
    a quick connect cryogen tank adapter, the adapter including
       a pin valve receiver portion,
       a post, and
       a lever,
       wherein the pin valve receiver portion receives a pin valve of a cryogen tank and actuating the lever moves the post to press on a pin in a pin valve of the cryogen tank to open the pin valve to allow the cryogen to flow into the flow path assembly.

11. A portable cryosurgical device of claim 10, wherein the adapter further includes:
    a vent that allows the cryogen in the flow path between the adapter and the solenoid valve to vent.

12. A portable cryosurgical device of claim 1, wherein the cryogen source is a single refillable cylinder with an amount of liquid cryogen from twelve ounces to twenty ounces.

13. A portable cryosurgical device of claim 1 further comprising:
    a cryogen source level indicator that provides an indication of an amount of the cryogen remaining in the cryogen source.

14. A portable cryosurgical device of claim 1, wherein the cryogen is at least one of liquid carbon dioxide, nitrous oxide, R125, and R410A.

15. A portable cryosurgical device of claim 1, wherein the cryogen is a liquefied compressed gas at a pressure of up to 850 psi.

16. A portable cryosurgical system of claim 1, wherein the flow path assembly further includes:
    an in-line cryogen filter that blocks foreign material from entering the valve while allowing the cryogen to flow freely.

17. A portable cryosurgical system of claim 1, wherein a volume of the cryogen in the flow path assembly is at a substantially same pressure as liquified compressed gas received from the cryogen source, and wherein the flow path assembly delivers the liquefied compressed gas from the cryogen source to a terminal end of the cryogen flow tube without a phase change occurring in the flow path.

18. A portable cryosurgical device of claim 1, wherein the cryogen is at least one of R125 and R410A.

19. A portable cryosurgical system of claim 1, wherein the inlet side of the valve seat and the outlet side of the valve seat are positioned in fluid communication with the cryogen flow tube to substantially instantaneously stop delivery of the cryogen to the target treatment area upon deactivation of the device.

\* \* \* \* \*